United States Patent [19]
Delignieres et al.

[11] Patent Number: 5,680,220
[45] Date of Patent: Oct. 21, 1997

[54] DEVICE AND METHOD FOR OPTICALLY MEASURING THE CHARACTERISTICS OF A SUBSTANCE UTILIZING THREE WAVELENGTHS OF LIGHT

[75] Inventors: Robert Delignieres, Mareil-Marly; Christian Durand, Marly Le Roi, both of France

[73] Assignee: Institut Francais du Petrole, Rueil Malmaison, France

[21] Appl. No.: 307,782

[22] PCT Filed: Jan. 31, 1994

[86] PCT No.: PCT/FR94/00120

§ 371 Date: Jan. 27, 1995

§ 102(e) Date: Jan. 27, 1995

[87] PCT Pub. No.: WO94/18543

PCT Pub. Date: Oct. 18, 1994

[30] Foreign Application Priority Data

Feb. 9, 1993 [FR] France .................. 93 01513

[51] Int. Cl.[6] .................. G01N 21/25; G01J 3/46
[52] U.S. Cl. .................. 356/406; 356/408; 356/414; 356/416; 356/419; 356/420; 356/425
[58] Field of Search .................. 356/406–408, 356/414, 416, 419–420, 425

[56] References Cited

U.S. PATENT DOCUMENTS

| | | | |
|---|---|---|---|
| 3,292,484 | 12/1966 | Clay | 356/408 |
| 3,999,864 | 12/1976 | Mutter | 356/416 |
| 4,125,329 | 11/1978 | French et al. | 356/408 |
| 4,367,041 | 1/1983 | Webb, Jr. et al. | 356/407 |
| 4,381,894 | 5/1983 | Gogol, Jr. et al. | 356/407 |
| 4,455,084 | 6/1984 | Webb, Jr. et al. | 356/407 |
| 4,624,571 | 11/1986 | Salda et al. | 356/406 |
| 5,357,343 | 10/1994 | Lowne et al. | 356/419 |
| 5,386,295 | 1/1995 | Switalski et al. | 356/419 |
| 5,387,977 | 2/1995 | Berg et al. | 356/406 |
| 5,418,614 | 5/1995 | Brost et al. | 356/408 |

*Primary Examiner*—David C. Nelms
*Assistant Examiner*—Jason D. Vierra Eisenberg
*Attorney, Agent, or Firm*—Antonelli, Terry, Stout & Kraus, LLP

[57] ABSTRACT

A first embodiment of the invention includes a light source (1) lighting two parallel optical branches (b1, b2) controlled respectively by two optical shutters (4, 6), one comprising a transparent cell (3) containing a substance to be studied, and the other being used to divert the light from the source. The light coming successively from one and from the other branch is applied selectively to three color filters (F1–F3) filtering three wavelengths selected according to the substance to be studied. The successive luminous intensities which have crossed each of the filters are measured through three detectors (D1 to D3) and the measurings are combined by means of a control (0). Analogous measuring sequences may be achieved with an embodiment comprising three light sources and a single detector. The device can be used for determination of the pH value of a substance.

16 Claims, 5 Drawing Sheets

DEVICE AND METHOD FOR OPTICALLY MEASURING THE CHARACTERISTICS OF A SUBSTANCE UTILIZING THREE WAVELENGTHS OF LIGHT

FIELD OF THE INVENTION

The present invention relates to a method and device for measuring optically the characteristics of a substance, such as, for example, the absorbance thereof.

BACKGROUND OF THE INVENTION

In the French patent FR-A-2,689,636 there is described a device for measuring the true optical absorbance of a substance contained in a cell. By means of optical switching means, light from a light source such as a halogen lamp whose frequency spectrum is known is transmitted successively to three optical filters of determined respective wavelengths. The first one corresponds to the isobestic point of the colored substance where the absorbance of the basic fraction of the substance is equal to that of its acid fraction and therefore independent of the pH value. The second one is in a part of the spectrum where the substance reacts most to the variations of the parameter to be measured. The third one is in a part of the spectrum where the absorbance of the substance substantially undergoes no variation. The light from each of the filters is so directed that it runs alternately through the cell containing the substance to be analyzed and an optical by-pass branch including for example a neutral filter, an optical by-pass fiber, or a reference cell, etc. The intensity of the successive emergent rays is measured and the various measurements are processed by a management and computing unit which determines optical characteristics of the substance, such as the true absorbance, which are independent of the possible fluctuations of the light source.

The method used provides accurate and reliable results, but the device implementing the method is relatively costly since it includes several optical switches whose unit price is relatively high.

SUMMARY OF THE INVENTION

The object of the invention is also to measure optical characteristics of a reacting substance contained in a transparent cell, such as its true absorbance, but the embodiment thereof is more simple and less costly than the prior art. It includes at least a light source, a first optical branch and a second optical branch allowing selectively passage of the light through the cell and outside it, an optical system for forming rays crossing the first optical branch and the second optical branch and a selective optical filter from an array of three selective filters, the first being centered on a first wavelength corresponding to the isobestic point of the reacting substance, the second one on a wavelength in a part of the light spectrum where the substance is the most sensitive, and the third one in another part of the spectrum where the substance is the least sensitive, means for measuring the intensity of the light crossing the optical system, a controller, and selection means controlled by said control set and an electric power pack.

The device is characterized by the selection means consisting of two optical shutters located respectively in the first branch and in the second branch, and of electric switching means.

The controller includes for example a control processor, an acquisition unit for acquiring the luminous intensity measuring signals and an interface set for controlling the selection means.

A first embodiment includes a single light source lighting the two branches and the optical system comprises by-pass means for directing towards the three filters the light rays which have crossed the first or the second branch, the measuring means include three detectors for measuring the light rays which have crossed the three filters, the electric means comprise elements for connecting intermittently the detectors to the controller set and a switch for connecting intermittently the lamp to the power pack.

According to another embodiment, the device includes three light sources, the optical system comprises by-pass means for directing the light from the sources respectively through the three selective filters and dividing means for applying the filtered light to the first and the second branches, the measuring means include, a single detector for measuring the light coming from one or from the other branch, and the electric switching means include elements for supplying selectively one of the three light sources.

The second optical branch includes for example an optical fiber associated with a neutral filter or a cell identical to the first one and containing a neutral substance.

The measuring method according to the invention when using the first embodiment of the invention includes achieving measuring cycles under the control of the controller, each cycle comprising:

- a first measuring stage for directing light having crossed the cells successively through the three filters and measuring the light intensities coming from the three filters;
- a second measuring stage for directing light which has crossed the second optical branch successively through the three filters and measuring the light intensities coming from the three filters; and
- combining of the intensity values measured by each detector respectively by the first and second stages for determining the characteristics of the reacting substance.

When using the second embodiment of the invention, each measuring cycle may also comprise:

- a measuring stage for directing the light which has crossed successively the three filters towards the cell containing the reacting substance and measuring respective light intensities,
- a measuring stage for directing the light which has crossed successively the three filters towards the second optical branch and measuring the respective light intensities; and
- a combining of the light intensity values coming from the light source for determining the characteristics of the reacting substance.

Whatever the embodiment used, the invention includes only two optical shutters, the sequence of the comparative measuring operations necessary for the acquisition of the measurements being controlled by electric switches which are easily achieved. The cost and the reliability of the invention are therefore significantly improved.

In order to improve further the measuring precision, the device may also comprise means for measuring the ambient temperature and the supply voltage of each lamp.

BRIEF DESCRIPTION OF THE DRAWINGS

Other features and advantages of the invention will be clear from reading the description hereafter of two embodiments given by way of non limitative example, with reference to the accompanying drawings in which.

DESCRIPTION OF THE PREFERRED EMBODIMENTS

Figure 1:
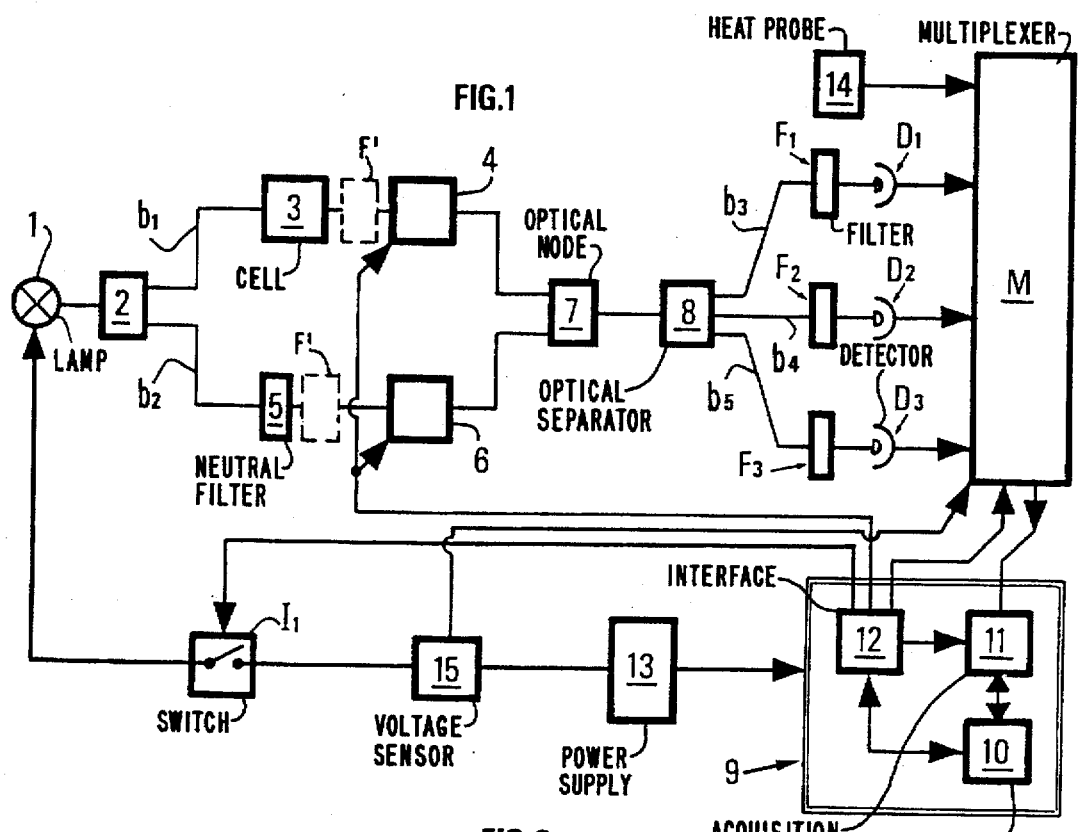
FIG.1 diagrammatically shows a first embodiment of the invention with a single source and a selective filtering achieved on the emergent light.

It should first be reminded that the pH value of a solution is calculated through the relation:

$$pH = pKi + \log x/(1-x) \quad (1),$$

where pKi is a constant and x is the basic fraction of the substance. This parameter x is related to the absorbance A of the substance by the relation $$x = A/(c \cdot l \cdot \pounds) \quad (2)$$

where c is the concentration, l is the length of the optical path crossed by the rays and £ is the extinction coefficient of the cell. The absorbance is expressed as a function of the incident intensity Ii applied to the cell and of the intensity Ie emerging therefrom, through the relation:

$$A = \log \frac{Ii}{Ie} \quad (3)$$

The values of the absorbance A are subject to large fluctuations if Ie is measuring only, on account of the lamp instability. In fact, it is well known that the characteristics of such a source vary with time. The color temperature for example is likely to change because of various causes due to the lamp itself: progressive vaporization of the filament, aging of the casing, etc, and to the instability of the power supply. This results in a notable modification in the form of the frequency spectrum of the source. It may for example be observed that the color temperature of the source may decrease in time by more than 10%, which leads to high ratio variations between the luminous intensities applied to the various filters, and consequently to measuring errors.

On account of its structure and of its implementation procedure, the invention precisely allows the characteristic variations in time of the source to be disregarded.

The first embodiment includes a light source 1 such as a halogen lamp with a tungsten filament. The light coming from source 1 is subdivided by an optical separator 2 into two light pencils which are directed by means of optical fibers b1, b2 for example, the first one towards a main optical branch including a cell 3 containing a reacting substance whose color variations are to be measured, followed by a first optical shutter 4, the second one towards a bypass optical branch to form a beam passing outside cell 3. This bypass branch comprises for example a neutral filter 5 whose transmittance is selected substantially equal to the average transmittance of cell 3, followed by a second optical shutter 6. The outputs of the two switches 4, 6 are connected to an optical node 7.

The light beam from the optical node 7, coming selectively from one or the other branch, is also subdivided by an optical separator 8 into three beams which are directed by three optical fibers b3, b4, b5 respectively towards three color filters F1, F2, F3. These three filters pass respectively the wavelengths 494 nm, 600 nm and 730 nm for example. The first one, F1, corresponds to the point known as isobestic point of the colored substance where the absorbance of the basic fraction of the substance is equal to that of its acid fraction and therefore independent of the pH value. The second, F2, is that for which the colored substance reacts most to the variations of the parameter to be measured. The third one, F3, corresponds to a wavelength for which the absorbance of the colored substance undergoes no variation. Each one of the three filters F1, F2, F3 works for example with a neutral filter F1 whose transmittance is selected so as to balance the luminous intensities passing through the three branches b3, b4, b5. The light having crossed respectively the three color filters F1, F2, F3 is applied to three photoelectric detectors D1, D2, D3. The signals delivered thereby are applied to three inputs of a multiplexer M.

The device is managed by a controller 9 including a control processor 10, an acquisition unit 11 connected to the output of multiplexer M and an interface 12 for controlling the optical shutters 4, 6 and multiplexer M. The device further comprises a power supply 13 such as a electrical storage in the case of an autonomous working of the device, this power supply being connected to lamp 1 by means of a switch I1 also controlled by interface 12. Preferably, the device also includes a heat probe 14 arranged next to the elements of the device to measure the ambient temperature, this probe being connected to an input of multiplexer M, as well as a voltmeter for measuring the voltage delivered by power supply 13.

Shutter 4 or 6 and the associated element 3 or 5 may be easily inverted in each of the branches b1, b2.

The measuring method allows the possible luminous intensity fluctuation of the source to be disregarded by determining each absorbance value from measurements achieved by a single detector.

Figure 3:
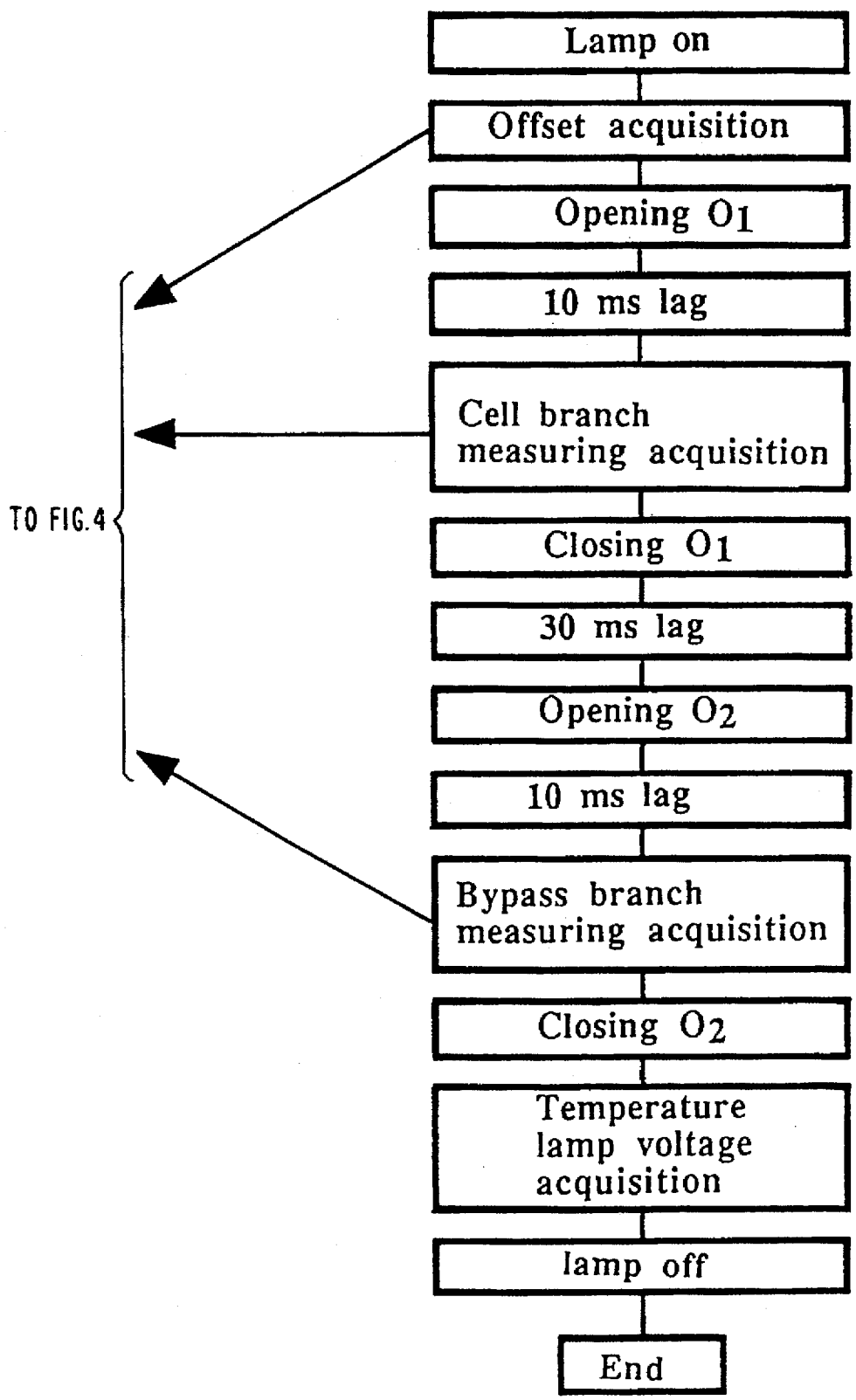
FIG.3 shows a flowchart example for the implementation of the embodiment of FIG. 1, FIG.4 details the stage of acquisition of the measurements in the flowchart of FIG.3.
Figure 4:
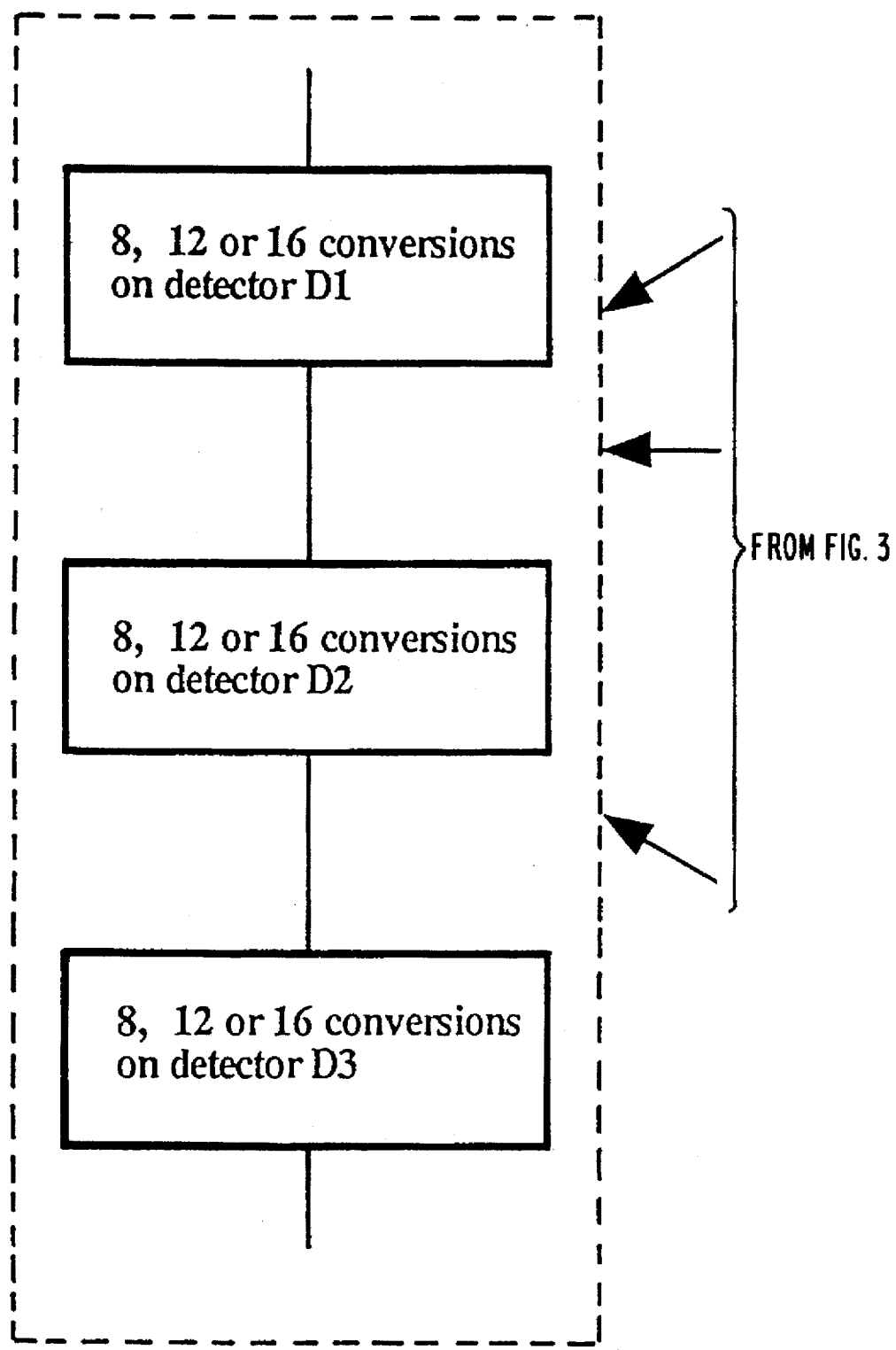

As shown by the flowcharts in FIGS.3, 4, each measuring cycle first comprises switching on of lamp 1 by the closing of switch I, followed by a series of 8, 12 or 16 measurings called "offset" measurings during which, shutters 4 and 6 are closed, the noise signals affecting detectors D1, D2, D3 are measured in sequence through a sequential control of multiplexer M, these signals being acquired and digitized by acquisition set 11. When the noise signals have been measured, shutter 4 is opened and a sequence of measurings of the light crossing cell 3 on the main branch b1 and successively being filtered through filters F1, F2, F3 is performed. After opening shutter 6 and by performing an analogous sequence, measurements of the incident light from the source which has crossed the neutral filter 5 of bypass branch b2, then successively filters F1 to F3, are acquired thereafter. To complete the previous measurings, an acquisition of the temperature measured by heat probe 14 and of the voltage applied to lamp 1 and measured by element 15 is preferably achieved.

The absorbances A1, A2 and A3 corresponding to the three wavelengths of the color filters F1 to F3 are calculated from the intensities of the light passing through the main branch containing cell 3 and through the bypass branch containing neutral filter 5. By applying relation (2), it may be shown that the value of the basic fraction x of the substance studied is obtained through the following relation:

$$x = k \cdot (A2 - A3)/(A1 - A3)$$

where k is a constant, and that, on account of the comparative method used, any degradation in time of the characteristics of lamp 1 is totally disregarded. Processor 10 may for example deduce therefrom the pH value of the analyzed substance.

The temperature and the effective voltage applied to lamp 1 are preferably taken into account so as to minimize errors. In fact, it may be noted that measuring errors are of the order of 4% when the temperature rises from 20° C. to 60° C. To compensate these variations, processor 10 applies to the measurements a correction according to the temperature variation, such as a linear correction for example.

In order to minimize measuring errors further, the voltage variations (due to the discharge of the accumulator in case of self-contained electrical supply), which cause the luminous intensity of lamp 1 to vary, may also be taken into account. Accurate measurements to within 1% may be obtained by taking these variations in temperature and in voltage into account.

The previous embodiment is suitable if the cell contains a coloring agent which is not substantially affected by being lit directly by lamp 1 and by receiving thereby the entire light spectrum.

Figure 2:
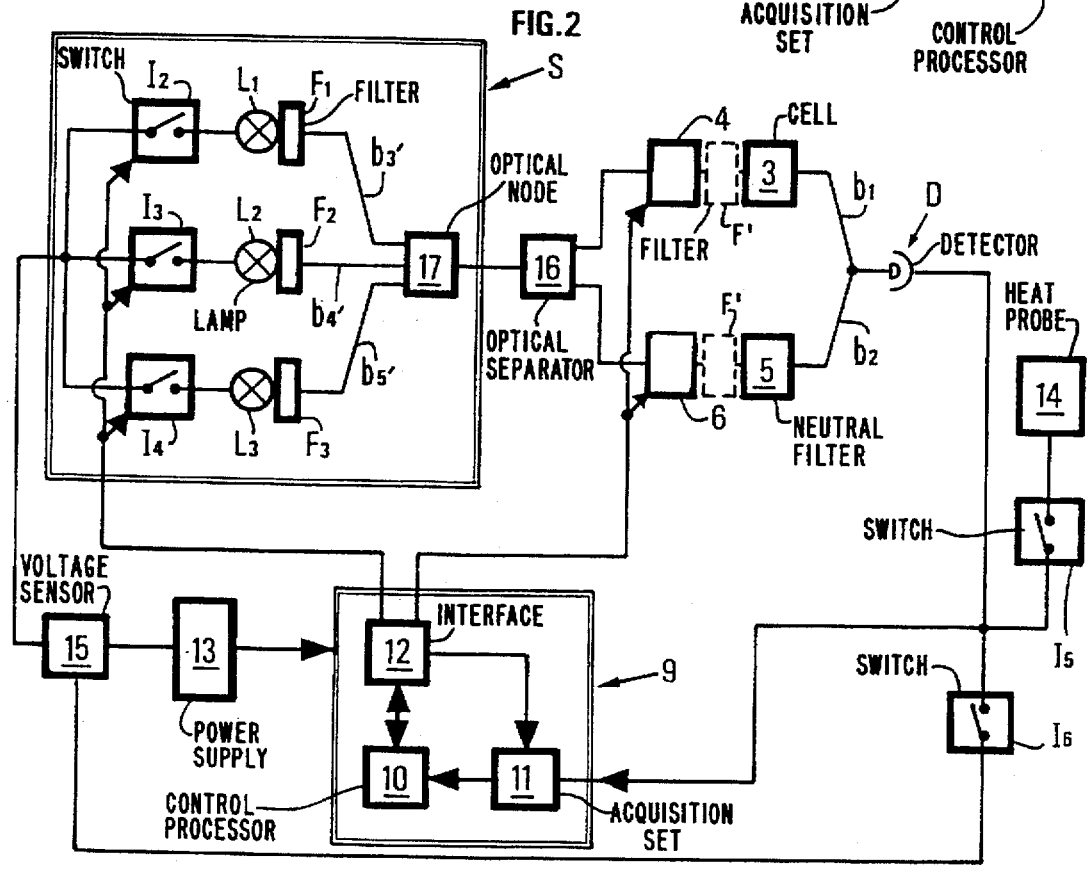
FIG.2 diagrammatically shows a second embodiment of the invention with a selective lighting of the cell by means of three different beams.

In the opposite case, it is preferable to use the embodiment of FIG.2. In this instance, the main branch 11 consisting of cell 3 and optical shutter 4, and the bypass branch including for example a neutral fiber are connected to an optical separator 16 linked to an optical selection means S with three branches b'3, b'4, b'5. Each one of them includes a lamp, respectively L1, L2, L3, analogous to lamp 1 (FIG. 1), which are connected to power supply 13 respectively by three switches I2, I3, I4 controlled by interface circuit 12. The light of these lamps is filtered respectively by the previous three color filters F1, F2, F3 which work for example with a neutral filter F1. The light filtered by the three color filters is directed, via an optical node 17, towards the input of the optical separator 16. The light coming from the two branches b1, b2 is applied to a single photoelectric detector D. A heat probe 14 is also connected to the input of acquisition unit 11 by means of a switch I5 controlled by interface set 12. Similarly, a voltmeter 15 for measuring the voltage applied to lamps L1 to L3 is interposed between the lamps and power supply 13, the signal of the voltmeter being applied to acquisition unit 11 by means of a switch I6.

Figure 5:
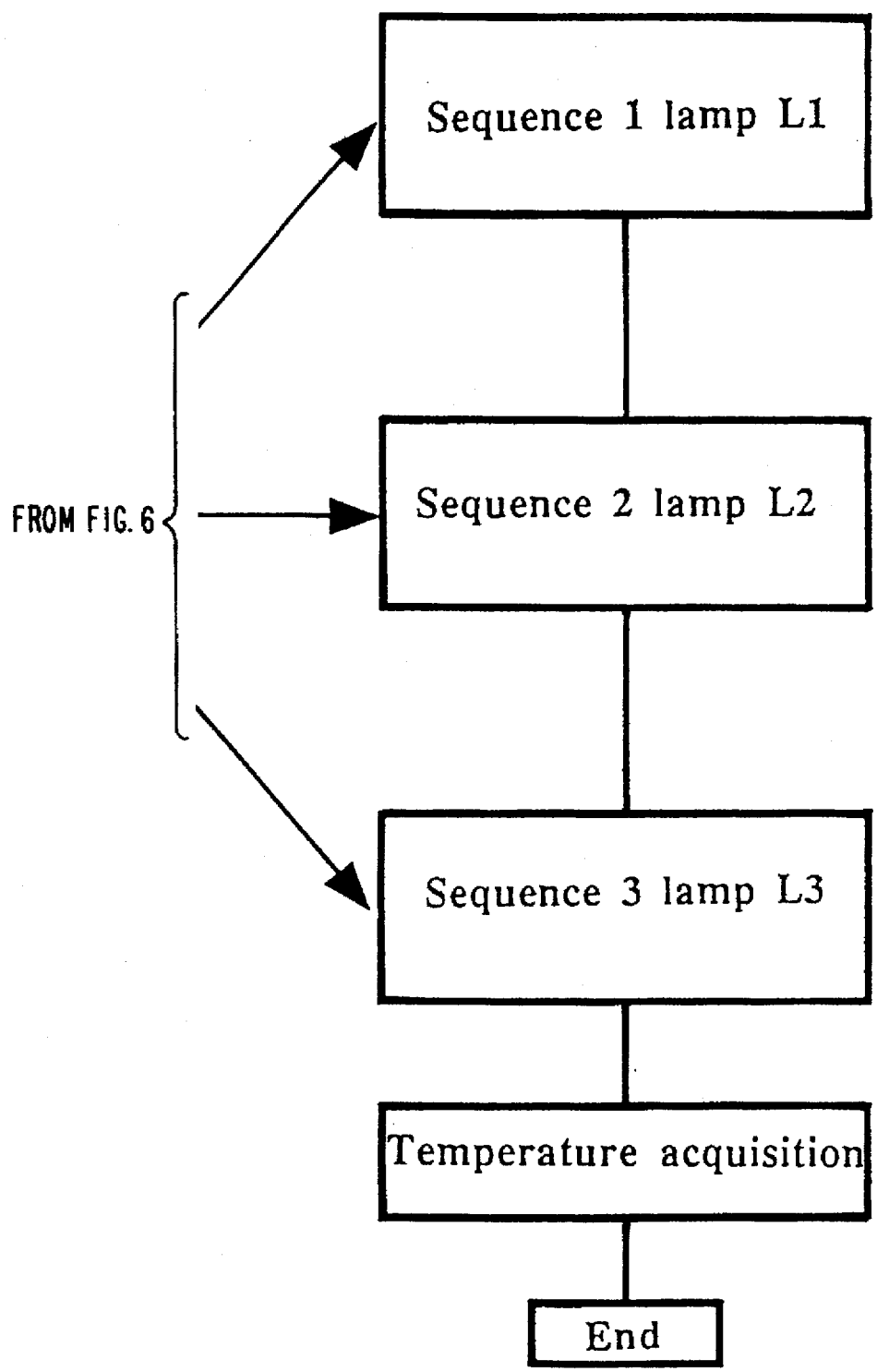
FIG.5 shows a flowchart example for the implementation of the embodiment of FIG.2.
Figure 6:
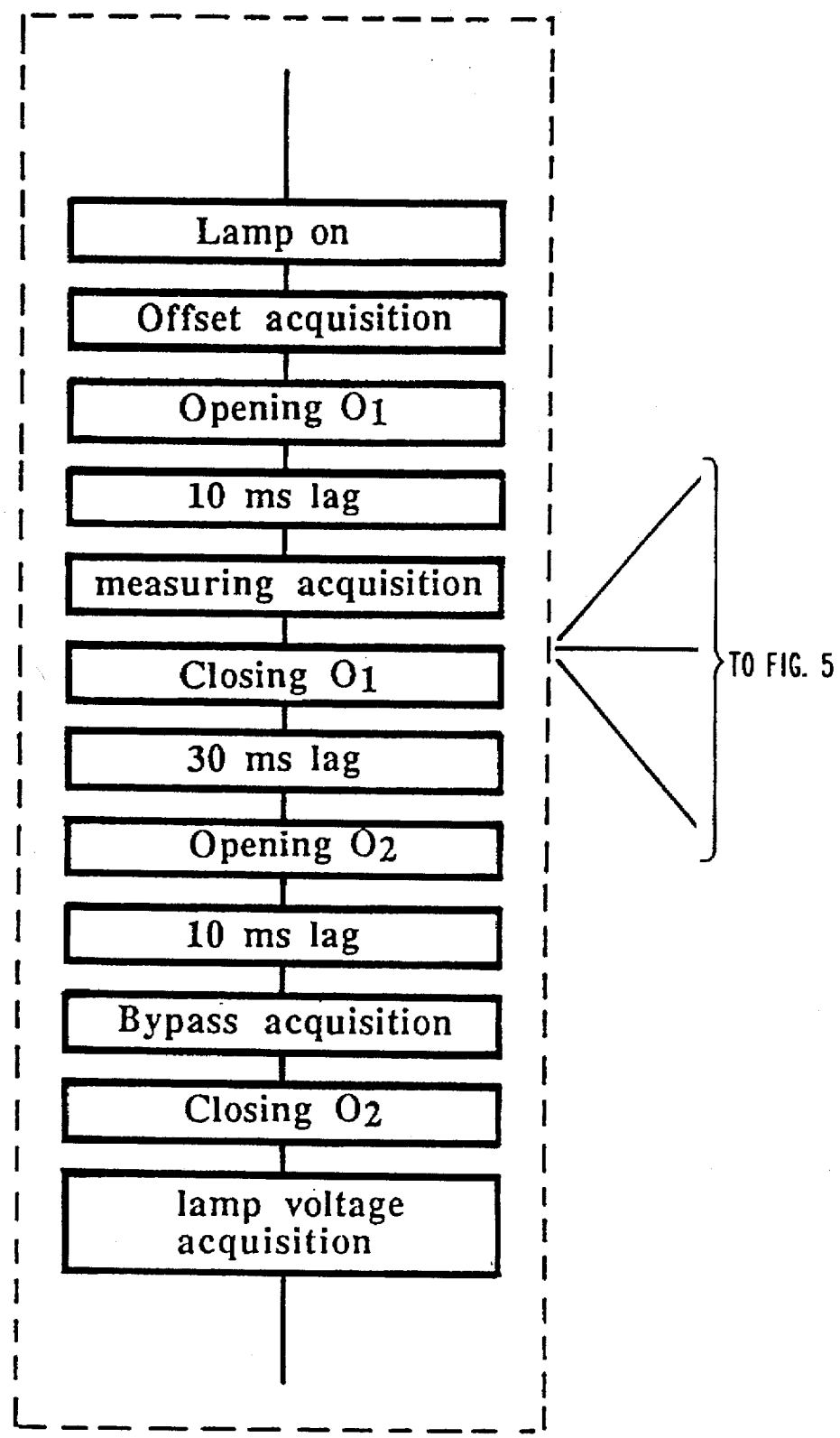
FIG.6 details the operations achieved for each lamp.

With this embodiment, each measuring cycle comprises (FIGS.5, 6) three identical sequences implementing successively lamps L1, L2 and L3. Each of the successive sequences comprises the switching on of the corresponding lamp, L1 for the first one for example, and, shutters 4 and 6 being closed, the signal delivered by the single photoelectric detector D in the absence of light is acquired (offset voltage). Then, during a first opening time interval of shutter 4, several successive measurings of the signal of detector D are performed. The previous operation is repeated for lamps L2 and L3 successively. Each sequence ends with an acquisition of the voltage measured by volmeter 15. After the three previous sequences, each cycle is ended by an acquisition of the ambient temperature measured by heat probe 14. As previously, the luminous intensity measurements are combined to obtain the absorbance values in cell 3 which is for example deduced therefrom.

The various optical branches or paths allowing the light to be directed through cell 3, neutral filter 5 and the color filters may consist of optical fibers, but they may also be obtained with conventional optical convergence or divergence means ("overhead" optics).

Without departing from the scope of the invention, the neutral filter used for forming the reference medium may be replaced by a cell analogous to cell 3 but containing a neutral substance so selected that the absorbance of this parallel cell is equal to the average absorbance of the main cell.

We claim:

1. A device for optically measuring modifications in a reacting substance contained in a transparent cell, comprising:

a single light source provided with an electric supply voltage and a specified light spectrum, a first optical circuit, a first optical shutter arranged in said first optical circuit, a second optical circuit, a second optical shutter arranged in said second optical circuit, an optical diverter in said optical circuits for diverting incident light from the single light source through the cell and through a reference medium to an optical node, an optical separator for directing light from the optical node to three other optical circuits, a set of three selective filters arranged respectively in said three other optical circuits, a first selective filter from the set being centered on a first wavelength corresponding to an isobestic point of the reacting substance, a second selective filter from said set being centered on a wavelength in a part of the light spectrum where the reacting substance is the most sensitive and a third selective filter from the set being centered on another part of the light spectrum where the reacting substance is the least sensitive, a measuring means for respectively measuring the light emanating from said three other optical circuits, including a set of three detectors for respectively detecting light passed by each of the set of three filters and producing output signals representing the detected light, an electric power supply for providing the electrical supply voltage, a controller and an electric switching means controlled by the controller for connecting intermittently said three detectors to said controller, for connecting the single light source to the power supply, and for selectively switching said optical shutters.

2. A device in accordance with claim 1 wherein the controller includes a controller microprocessor, an acquisition unit for acquiring the output signals and an interface for controlling the selection means.

3. A device in accordance with claim 1 further comprising means for measuring an ambient temperature and producing a signal representing the ambient temperature coupled to the controller.

4. A device in accordance with claim 1 further comprising means for measuring a supply voltage of each lamp and producing a signal representing the supply voltage of each lamp coupled to the controller.

5. A device in accordance with claim 1 wherein the second optical branch comprises a neutral filter.

6. A device in accordance with claim 1 wherein the second optical branch comprises another cell substantially identical to the cell and containing a neutral substance.

7. A device in accordance with claim 1 wherein the first optical branch and the second optical branch each comprise at least one optical filter.

8. A device for optically measuring modifications in a reacting substance contained in a transparent cell, comprising:

a first optical branch and a second optical branch, an optical director for selectively directing an incident light beam through the cell of a first optical branch and through a reference medium of a second optical branch, a measuring means including a single detector for measuring light passing through the first or second optical branch and producing output signals representing the detected light, a controller coupled to the output signals including a microprocessor, an electric power supply providing an electrical supply voltage, a selection means including optical shutters arranged respectively in the first optical branch and in the second optical branch, an electric switching means controlled by the controller, for selectively switching the optical shutters to selectively pass the incident light through the first and second optical branches, three light sources provided with a specified light spectrum, a set of three selective filters arranged respectively in three optical circuits, a first selective filter from the set being centered on a first wavelength corresponding to an isobestic point of the reacting substance, a second selective filter from said set being centered on a wavelength in a part of the light spectrum where the reacting substance is the most sensitive and a third selective filter from the set being centered on another part of the light spectrum where the reacting substance is the least sensitive, said three filters being respectively associated with the three light sources.

9. A device in accordance with claim 8 wherein the controller includes an acquisition unit for acquiring the output signals and an interface for controlling the selection means.

10. A device in accordance with claim 8 further comprising means for measuring an ambient temperature and producing a signal representing the ambient temperature coupled to the controller.

11. A device in accordance with claim 8 further comprising means for measuring a supply voltage of each lamp and producing a signal representing the supply voltage of each lamp coupled to the controller.

12. A device in accordance with claim 8 wherein the second optical branch comprises a neutral filter.

13. A device in accordance with claim 8 wherein the second optical branch comprises another cell substantially identical to the cell and containing a neutral substance.

14. A device in accordance with claim 8 wherein the first optical branch and the second optical branch each comprise at least one optical filter.

15. A method for optically measuring modifications in a reacting substance contained in a transparent cell, with a device having a single light source provided with an electric supply voltage and specified light spectrum, a first optical circuit, a first optical shutter arranged in said first optical circuit, a second optical circuit, a second optical shutter arranged in said second optical circuit, an optical diverter in said optical fiber circuits for diverting incident light from the single light source through the cell and through a reference medium to an optical node, an optical separator for directing light from the optical node to three other optical circuits, a set of three selective filters arranged respectively in said three other optical circuits, a first selective filter from the set being centered on a first wavelength corresponding to an isobestic point of the reacting substance, a second selective filter from said set being centered on a wavelength in a part of the light spectrum where the reacting substance is the most sensitive and a third selective filter from the set being centered on another part of the light spectrum where the reacting substance is the least sensitive, a measuring means for respectively measuring the light emanating from said three other optical circuits, including a set of three detectors for respectively detecting light passed by each of the set of three filters and producing output signals representing the detected light, an electric power supply for providing the electrical supply voltage, a controller and an electric switching means controlled by the controller for connecting intermittently said three detectors to said controller, for connecting the single light source to the power supply, and for selectively switching said optical shutters comprising:

directing light during a first stage passing through the cell successively through the three filters and measuring light intensities outputted from the three filters;

directing light during a second stage passing through the second optical branch successively through the three filters and measuring the light intensities coming from the three filters; and combining the light intensity values measured by each detector respectively from the first and second stages for determining characteristics of the reacting substance.

16. A method for optically measuring modifications in a reacting substance contained in a transparent cell, with a device including a first optical branch and a second optical branch, an optical director for selectively directing an incident light beam through the cell of a first optical branch and through a reference medium of a second optical branch, a measuring means including a single detector for measuring light passing through the first or second optical branch and producing output signals representing the detected light, a controller coupled to the output signals including a microprocessor, an electric power supply providing an electrical supply voltage, a selection means including optical shutters arranged respectively in the first optical branch and in the second optical branch, a switching means controlled by the controller, for selectively switching the optical shutters to selectively pass the incident light through the first and second optical branches, three light sources provided with a specified light spectrum, a set of three selective filters arranged respectively in three optical circuits, a first selective filter from the set being centered on a first wavelength corresponding to an isobestic point of the reacting substance, a second selective filter from said set being centered on a wavelength in a part of the light spectrum where the reacting substance is the most sensitive and a third selective filter from the set being centered on another part of the light spectrum where the reacting substance is the least sensitive, said three filters being respectively associated with the three light sources comprising:

directing light during a first stage passing successively through the three filters towards the cell containing the reacting substance and measuring respective light intensity values;

directing light during a second stage passing successively through the three filters towards the second optical branch and measuring respective light intensity values; and combining the light intensity values from the first and second stages for determining characteristics of the reacting substance.

* * * * *